US012582747B2

(12) United States Patent
Sander et al.

(10) Patent No.: US 12,582,747 B2
(45) Date of Patent: Mar. 24, 2026

(54) IMPLANTABLE BIOMATERIAL, AND METHOD OF MANUFACTURING THEREOF

(71) Applicant: University of Galway, Galway (IE)

(72) Inventors: Elizabeth Sander, Galway (IE); William Hickey, Tipperary (IE); Robert Pendlebury, Mayo (IE); Faisal Sharif, Galway (IE); Brendan Marrinan, Galway (IE); Tony O'Halloran, Galway (IE)

(73) Assignee: University of Galway, Galway (IE)

( * ) Notice: Subject to any disclaimer, the term of this patent is extended or adjusted under 35 U.S.C. 154(b) by 1052 days.

(21) Appl. No.: 17/266,227

(22) PCT Filed: Aug. 7, 2019

(86) PCT No.: PCT/EP2019/071171
§ 371 (c)(1),
(2) Date: Feb. 5, 2021

(87) PCT Pub. No.: WO2020/030670
PCT Pub. Date: Feb. 13, 2020

(65) Prior Publication Data

US 2021/0299324 A1 Sep. 30, 2021

(30) Foreign Application Priority Data

Aug. 7, 2018 (EP) .................................... 18187715

(51) Int. Cl.
*A61L 27/18* (2006.01)
*A61L 27/50* (2006.01)
*B29C 43/00* (2006.01)
*B29K 75/00* (2006.01)
*B29L 31/00* (2006.01)

(52) U.S. Cl.
CPC ............. *A61L 27/18* (2013.01); *A61L 27/507* (2013.01); *B29C 43/003* (2013.01); *A61L 2430/20* (2013.01); *B29K 2075/00* (2013.01); *B29L 2031/7534* (2013.01)

(58) Field of Classification Search
None
See application file for complete search history.

(56) References Cited

U.S. PATENT DOCUMENTS 3,963,681 A * 6/1976 Kaneko .................. C08G 18/12 528/61
4,465,480 A 8/1984 Tanaka et al.
2003/0109923 A1* 6/2003 Chinn ................... A61F 2/2412 623/2.4
2005/0025966 A1 2/2005 Vedula et al.
2005/0255082 A1* 11/2005 Santerre ................. A61K 47/60 424/78.3
2007/0027528 A1 2/2007 Agnew
2010/0152405 A1 6/2010 Sunkara
2013/0089582 A1* 4/2013 Nielsen ...................... C08J 3/24 522/174
2013/0115466 A1 5/2013 Madsen et al.

FOREIGN PATENT DOCUMENTS

JP 2007007838 A 1/2007
KR 100240437 B1 * 1/2000 ............. C08G 18/48
WO 9924084 A1 5/1999

OTHER PUBLICATIONS

Liu, X., Wang, T., Li, J. et al. Synthesis and properties of segmented polyurethanes with hydroquinone ether derivatives as chain extender. J Polym Res 22, 149 (2015). https://doi.org/10.1007/s10965-015-0792-5 (Year: 2015).*
S.N. Tong, S.R. Tsai, J.S. Lii, and P.T.K. Wu. Aromatic Diols as Chain Extender in PU Reaction Molding, Journal of Elastomers & Plastics 1987 19:3, 188-203. https://doi.org/10.1177/009524438701900304 (Year: 1987).*
Yildirim, E., Yurtsever, M., Yilgör, E., Yilgör, I. and Wilkes, G.L., Temperature-dependent changes in the hydrogen bonded hard segment network and microphase morphology in a model polyurethane: Experimental and simulation studies. J. Polym. Sci. Phys., 56: 182-192. https://doi.org/10.1002/polb.24532 (Year: 2018).*
Translation of Kim et al. KR20060124927A , Published Oct. 27, 1999. Machine translation by WIPO Retrieved from https://patentscope.wipo.int/search/en/detail.jsf?docId=KR1109961&_cid=P20-MHCGBZ-89388-1 (Year: 1999).*
International Search Report and Written Opinion in corresponding Application No. PCT/EP2019/071171, dated Nov. 27, 2019,(17 pages).

* cited by examiner

*Primary Examiner* — Ali Soroush
*Assistant Examiner* — Afua Bamfoaa Boateng
(74) *Attorney, Agent, or Firm* — Bookoff McAndrews, PLLC

(57) ABSTRACT

A method of forming an implantable biomaterial comprising the steps of providing a polyether-diisocyanate prepolymer, reacting the prepolymer with one or more chain extender molecules typically including benzene 1,4-diol to form a mouldable polymer selected from a polyurethane or polyurethane-urea polymer or a polyurethane-urea block copolymer; placing the mouldable polymer into an implantable biomaterial shaped mould, and shaping and curing the mouldable polymer in the implantable biomaterial shaped mould to form the implantable biomaterial. An implantable biomaterial such as a heart valve leaflet is also disclosed.

15 Claims, 3 Drawing Sheets

Monodentate urethane linkage Monodentate urea linkage Bidentate urea linkage

POLYURETHANE

POLYUREA

IMPLANTABLE BIOMATERIAL, AND METHOD OF MANUFACTURING THEREOF

CROSS-REFERENCE TO RELATED APPLICATION(S)

This patent application is the U.S. National Phase Entry under 35 U.S.C. § 371 of International Application No. PCT/EP2019/071171, filed on Aug. 7, 2019, which claims priority to EP Patent Application No. 18187715.0, filed on Aug. 7, 2018.

FIELD OF THE INVENTION

The present invention relates to an implantable biomaterial, and in particular a heart valve leaflet. The invention also relates to linear polymers and block copolymers useful for manufacturing the implantable biomaterial, and a method of manufacturing an implantable biomaterial from the linear polymers and block copolymers.

BACKGROUND TO THE INVENTION

When the human heart valve becomes diseased or dysfunctional, it requires either repairing or replacing. The proposed invention addresses the latter. For a replacement valve to be successful it must satisfy the following:

- Withstand at least 400 million opening and closing cycles at up to twice the normal heart rate
- Replicate the physiological behaviour of the natural human heart valve and integrate with the native environment with respect to the following:
- Blood flow
  - Biocompatibility
  - Thrombogenicity
  - Oxidative and hydrolytic degradation resistance
  - Demonstrate ease of use for the surgeons to handle and implant
  - Satisfy requirements of ISO 5840 Cardiovascular Implants—Cardiac Valve Prostheses The current major problem associated with tissue heart valve replacements, which emulate the natural heart valve haemodynamics better than mechanical valves, is they are not durable enough to withstand the lifespan of the patient beyond 15 years of implantation. Mechanical valves on the other hand, are able to last a patient's lifetime but require chronic anticoagulation. Consequently, the current invention proposes to solve this problem so that reliable flexible synthetic heart valve leaflets in place of tissue valve leaflets can be implanted and replicate the natural heart valve function while removing the requirement for lifelong anticoagulant therapy.

There are two types of valves presently used to replace existing heart valves: mechanical valves and bioprosthetic valves. Mechanical valves, typically made of pyrolytic carbon or titanium alloy, are easy to use and to implant, but they do not replicate physiological haemodynamics, which results in thrombosis and embolisms. Consequently, the patient requires anticoagulant therapy for the remainder of their lives. Additionally, the rigid body and leaflets require open heart surgical implantation and will not allow for percutaneous intervention. Bioprosthetic tissue heart valves reproduce the physiological flow characteristics of the native valve. As such, they are less thrombogenic compared to mechanical valves. However, they are less durable than mechanical heart valves and are prone to oxidative degradation and calcification. The type of flexible leaflet material in these valves is xenogenic biological tissue, typically from porcine valve tissue or bovine pericardium origin. Porcine valves and bovine pericardium are limited and unsustainable resources. Additionally, these xenogenic materials are expensive, limited by geography due to disease, and may result in variable quality of leaflets due to orientation of collagen fibers arranged within the pericardium. Even so, this xenogenic material is the only material used in commercially available flexible heart valves to date.

The key problem associated with polymeric heart valves is their biocompatibility. Previous polymeric heart valve attempts have largely failed due to calcification in vivo. The invention proposes to solve this by developing a more uniform molecular weight polymer with no oligomers, which can leach to the surface and promulgate calcification and degradation. This molecular weight distribution will also increase the fatigue resistance of the material, which will reduce the propensity for surface crazing and thrombosis.

There have been many investigations into the use of polymer materials as an alternative to existing bioprosthetic and mechanical leaflet materials. Despite many attempts at polyurethane-based material solutions, no polymer-based material solution for heart valve leaflets has successfully made it to the clinical market to date. Polymeric valve leaflet material investigations have been based around commercially available polyurethanes or polymers such as poly (styrene isobutylene styrene) (SIBS) and cross-linked poly (styrene isobutylene styrene) (xSIBS). However, the molecular weight distribution of these is large and variable, which can be exacerbated by any subsequent thermal process such as pelletising prior to moulding. SIBS-based polymers have poor mechanical properties and, as such, require reinforcement, or cross-linking, for load bearing applications. Their mechanical properties are also severely impacted by fluid uptake, even in very small amounts. In particular, most commercial polyurethanes use poly(tetramethylene oxide) as the polyol, which exhibits poor fatigue strength as the molecular weight decreases. Commercially available polymers such as Cardiothane 51 and Elast-Eon have also been investigated in the heart valve space. Some, such as Biomer, can exhibit reductions in their mechanical properties through mere contact with blood without experiencing any mechanical stress at all. A further disadvantage of many commercially available polyurethanes is that they are required to be melt-processable and thus result in structures with less hydrogen bonding.

US2010/152405 describes thermoplastic polyurethanes formed by reacting diisocyanate and polytrimethylene ether glycol to form a prepolymer, reacting the prepolymer with a diol chain extender and monofunctional alcohol or amine to form a reaction mixture and post curing the reaction mixture. U.S. Pat. No. 4,465,480 discloses a device for use in the body comprising a polyether polyurethane urea obtained by chain extension of an isocyanate-terminated prepolymer with a diamine. US2007/027528 describes a prosthetic valve comprising flexible valve inlets formed from a biocompatible polyurethane.

SUMMARY OF THE INVENTION

The Applicant has developed an implantable biomaterial comprising a linear polyurethane or polyurethane-urea polymer, or a polyurethane-urea block copolymer, in a two-step process, that has a hydrogen bonded and preferably a phase separated structure. The existence of hydrogen bonding in polyurethanes and polyureas increases the strength of the material but also assists in the development of a microphase separated morphology, particularly if the hydrogen bonding is largely within the hard segment phase. The development of this two-phase morphology is a critical requirement for fatigue resistance, but this process removes the ability of the material to be melted and reformed with the same properties. Consequently, the Applicant has provided a methodology and implantable material in which the morphology and associated hydrogen bonding is developed during the shaping of the implantable biomaterial such that strength and fatigue resistance are maintained. An advantage of the method of the invention is that, as it is produced by means of a two-step process using a prepolymer, the resultant molecular weight distribution is narrow, and the polymer also does not experience any melt shear, which can alter the molecular weight distribution and thus improves the biocompatibility. In addition, the two-step process provides a more consistent polymer because the polyol is not competing with the chain extenders for the free isocyanate groups. Primary amines have much higher reaction rates than primary hydroxyl groups and so a “one-shot” reaction could result in a very high molecular weight distribution polymer compared with the “two-shot” process. A higher molecular weight distribution could result in oligomers leaching out of the polymer, compromising the biocompatibility, and the resultant polymer would be weaker in terms of its mechanical properties. Another advantage of the method and polymer of the invention is that the mechanical properties are sufficient so that no reinforcement is necessary. The polymers produced according to the methods of the invention are all hydrogen bonded and exhibit good mechanical properties including tensile modulus and strength, good fatigue properties and good biocompatibility, with the block copolymers exhibiting tuneable mechanical properties based upon the degrees of polymerisation of the constituent blocks.

In one aspect, the Applicant has discovered that use of a specific chain extender, benzene 1, 4-diol (hydroquinone), alone or in combination with a second chain extender, gives a unique elastomer exhibiting a highly hydrogen bonded structure (Table 1) imparting thermosetting-like behaviour, and typically having an elastic modulus of 2 MPa to 6 MPa, or more specifically a modulus of 3 MPa to 5 MPa, that are mechanical properties specifically suited to the functional requirements of an implantable flexible material. The increased hydrogen bonding in the polymer confers a resistance to plastic deformation and a minimised hysteresis profile. These are essential characteristics in the context of implantable biomaterials, especially heart valve leaflets, which undergoes cyclic strain up to 20-30% over millions of cycles (heart beats) and need to recover their shape in response to elastic deformation without plastically deforming. The polymers of the invention have been tested in an accelerated manner up to 200 beats per minute and have been shown to recover their shape without plastic deformation (stretching) over time.

In a first aspect, the invention provides a method of forming an implantable biomaterial comprising the steps of:

- providing a polyether-diisocyanate prepolymer;
- reacting the prepolymer with one or more chain extender molecules to form a mouldable polymer selected from a polyurethane polymer, a polyurethane-urea polymer, and a polyurethane-urea block copolymer; and
- shaping and the mouldable polymer to form the implantable biomaterial.

In one embodiment, the mouldable polymer is cured, optionally during the shaping step.

In one embodiment, the mouldable polymer is shaped in an implantable biomaterial shaped mould. Other methods of shaping the mouldable polymer may be employed, for example solvent casting or electrospinning into a fibre.

In one embodiment, the mouldable polymer is cured in an implantable biomaterial shaped mould.

In one embodiment, the implantable biomaterial comprises a valve leaflet, suitable as a heart valve leaflet, and preferably an aortic, mitral, tricuspid or pulmonary heart valve leaflet.

In one embodiment, the polyether-diisocyanate comprises an aromatic diisocyanate, for example a toluene diisocyanate such as 2, 4 toluene diisocyanate.

In one embodiment, the polyether is selected from the group consisting of: poly(propylene glycol); poly(ethylene glycol); Poly(tetramethylene glycol); Hydroxyl terminated Poly(dimethyl siloxane); Hydroxy terminated polybutadiene; Polybutylene adipate and Polycaprolactone. In one embodiment, the polyether is selected from the group consisting of poly(propylene glycol) and poly(ethylene glycol).

In one embodiment, the prepolymer is reacted with two chain extender molecules, one of which comprises amine functionality and one of which comprises hydroxyl functionality; or the prepolymer is reacted with one chain extender molecule comprising both amine and hydroxyl functionality. In this embodiment, the implantable biomaterial formed in the process is a polyurethane-urea block copolymer.

In one embodiment, the or each chain extender is a linear aromatic molecule.

In one embodiment, the chain extender comprises one, two or all of p-phenylene diamine, benzene-1-4-diol, and 4-aminophenol. In one embodiment, the chain extender comprises p-phenylene diamine and benzene-1-4-diol, or 4-aminophenol. In one preferred embodiment, the chain extender comprises benzene 1,4-diol. In one preferred embodiment, the chain extender comprises benzene 1,4-diol and a second chain extender with amino functionality. In an especially preferred embodiment, the chain extender comprises p-phenylene diamine and benzene-1-4-diol, optionally in combination with another chain extender.

In one embodiment, a weight ratio of diisocyanate, polyether and chain extender in the block copolymer is 2-6:1-3:1-3 preferably about 2:1:1.

In one embodiment, the mouldable polymer is a thermosetting polymer.

In one embodiment, the method includes an initial step of reacting a polyether with a diisocyanate to form the polyether-diisocyanate polyurethane prepolymer. In one aspect, the components are reacted together in a weight equivalent ratio of about 0.5 to 1.5:0.5-1.5, preferably about 1:1.

In a second aspect, the invention also provides an implantable biomaterial, for example a heart valve leaflet, obtained or obtainable according to a method of the invention.

In a third aspect, the invention also provides a polymer of generally formula I, or an implantable biomaterial comprising or consisting essentially of the polymer of general formula I:

$$[X_1—[Y_1]n_1\text{-}X_2—Z_1]m_1\text{-}[X_1—[Y_2]n_2\text{-}X_2—Z_2]m_2 \qquad [I]$$

in which:

- $X_1$ and $X_2$ are each, independently, an (aromatic) diisocyanate, in which $X_2$ is optionally absent;
- $Y_1$ and $Y_2$ are each, independently, a polyether;
- $Z_1$ and $Z_2$ are each, independently, chain extender molecules;

$n_1$ and $n_2$ are each, independently, a whole number from 1 to 100; and $m_1$ and $m_2$ are each, independently, a whole number from 1 to 100.

In one embodiment, $X_1$ and $X_2$ are the same. In one embodiment, $X_1$ and $X_2$ are different.

In one embodiment, $Y_1$ and $Y_2$ are the same. In one embodiment, $Y_1$ and $Y_2$ are different.

In one embodiment, $X_1$ and $X_2$ are a toluene diisocyanate.

In one embodiment, $Y_1$ and $Y_2$ are poly(propylene glycol).

In one embodiment, $m_1$ and $m_2$ are each, independently, a number from 30 to 40.

In one embodiment, the polymer of general formula I has a structure of general formula II (below).

The polymer of general formula II is a polyurethane-urea block copolymer in which the polyether is poly(propylene glycol) and the chain extenders are a diamine (phenylene diamine) and a diol (hydroquinone). Implantable biomaterials formed from this polymer exhibit hydrogen bonded, microphase separated, morphology.

In one embodiment, the polymer of general formula I has a structure of general formula III (below).

The polymer of general formula III is a polyurethane polymer in which the polyether is poly(propylene glycol) and the chain extender is a diol (hydroquinone).

In one embodiment, the polymer of general formula I has a structure of general formula IV (below).

[II]
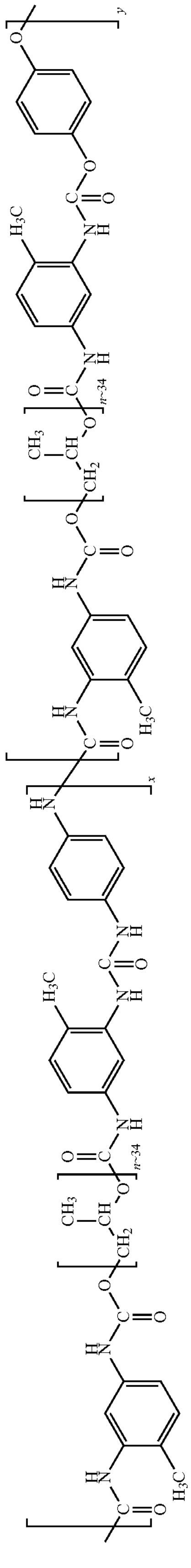
[III]
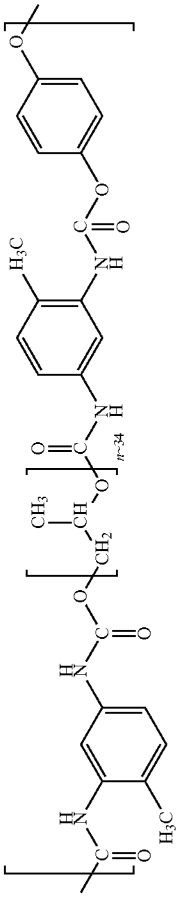
[IV]
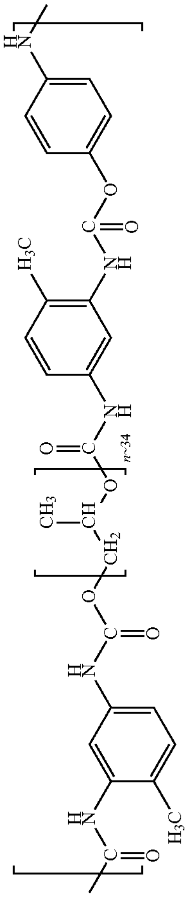

The polymer of general formula IV is a polyurea polymer in which the polyether is poly(propylene glycol) and the chain extender is a diamine (diphenylamine).

In one embodiment, the implantable biomaterial is a valve leaflet.

In a fourth aspect, the invention also provides a heart valve comprising a valve leaflet of the invention. In one embodiment, the valve is a percutaneously delivered valve.

In one embodiment, the polymer exhibits a narrow molecular weight distribution.

In one embodiment, the polymer does not exhibit melt shear.

In a sixth aspect, the invention also provides a method of forming a mouldable polymer comprising the steps of:

providing a polyether-diisocyanate prepolymer; and reacting the prepolymer with one or more chain extender molecules to form a mouldable polymer.

In one embodiment, the polyether diisocyanate comprises an aromatic diisocyanate, for example a toluene diisocyanate such as 2,4-toluene diisocyanate.

In one embodiment, the polyether is poly(propylene glycol) or poly(ethylene glycol).

In one preferred embodiment, the chain extender comprises benzene 1,4-diol. In one preferred embodiment, the chain extender comprises benzene 1,4-diol and a second chain extender with amino functionality. In an especially preferred embodiment, the chain extender comprises p-phenylene diamine and benzene-1-4-diol, optionally in combination with another chain extender. In one embodiment, the prepolymer is reacted with two chain extender molecules, one of which comprises amine functionality and one of which comprises hydroxyl functionality; or the prepolymer is reacted with one chain extender molecule comprising both amine and hydroxyl functionality. In one embodiment, the chain extender with hydroxyl functionality is benzene 1,4-diol.

In one embodiment, the or each chain extender is a linear aromatic molecule.

In one embodiment, the chain extender comprises one, two or all of p-phenylene diamine, benzene-1-4-diol, and 4-aminophenol. In one embodiment, the chain extender comprises p-phenylene diamine and benzene-1-4-diol, or 4-aminophenol.

In one embodiment, a weight ratio of diisocyanate, polyether and chain extender in the block copolymer is 2-6:1-3:1-3 preferably about 2:1:1.

The invention also provides a mouldable polymer formed according to the method of the invention, and an implantable device formed from the mouldable polymer.

In the methods of the invention, the or each chain extender molecule may be mixed with a solvent (typically a volatile solvent such as acetone, tetrahydrofuran, dimethylacetamide, or dimethylformamide) prior to reacting with the prepolymer. In one embodiment, a catalyst for the isocyanate reaction is added to the chain extender-solvent, for example an organic metal salt catalyst based on Sodium, Copper, Zinc, Chromium, Lead, Iron, Tin, Cobalt, Vanadium and Bismuth. In one embodiment, the catalyst is zinc neodecanoate.

The invention also relates to a method of treating a disease or condition associated with calcification of tissue in a subject comprising a step of replacing or augmenting the tissue with an implantable biomaterial or mouldable polymer according to the invention.

In one embodiment, the method includes an initial step reacting a polyether with a diisocyanate to form the polyether-diisocyanate prepolymer.

Other aspects and preferred embodiments of the invention are defined and described in the other claims set out below.

DETAILED DESCRIPTION OF THE INVENTION

Figure 1:
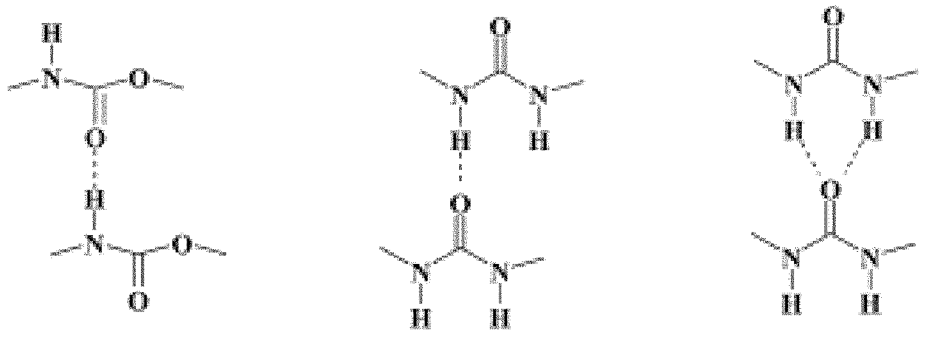
FIG. 1: Reaction of isocyanate and polyol for formation of urethane and urea bonds.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the replacement of tissue) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "polymer" refers to a polymer formed by reaction of a polyether-diisocyanate prepolymer with one or more suitable chain extender molecules (diol, diamine, or diol and diamine) to form mouldable polyurethane polymers (when the chain extender is a diol), mouldable polyurethane-urea polymers (when the chain extender is a diamine), or mouldable polyurethane-urea block copolymers (when the chain extender(s) comprise both diol and diamine functionality). The resultant structure has a diisocyanate-terminated polyol structure, preferably a toluene diisocyanate polypropylene glycol structure. Typically, the ratio of isocyanate groups to the reacting diol and/or diamine functional groups in 1:1. In one embodiment, the polymer exhibits a narrow molecular weight distribution. In one embodiment, the polymer does not exhibit melt shear. In one embodiment, the polymer of the invention is linear. As used herein, the term "linear" as applied to a polymer means that the polymer exhibits a linear, non-branched, structure. For the purpose of the invention, a linear polymer is created as this possesses less free volume compared with a non-linear polymer and it also allows for phase separation. Preparing polymers from isocyanate containing chemicals requires two functional isocyanate groups and linear polymers are formed when both chemicals have two functional groups as shown in FIG. 1 below. An isocyanate reacting with a hydroxyl group results in a urethane bond and an isocyanate reacting with an amine group results in a urea bond (FIG. 1). The maximum molecular weight of the polymer occurs when the ratio of the isocyanate groups to the reacting functional groups is or approximates to one, which it is in the invention. This is also preferable to ensure that there are no free isocyanate groups remaining in the final polymer. The polymers of the invention are generally not crosslinked, and the method generally do not require a crosslinking step. The polymer of the invention is typically formed using about 1.5 to 2.5 weight equivalents of diisocyanate, 0.5 to 1.5 weight equivalents of polyether, 0.5 to 1.5 weight equivalents of chain extender, and 1-5% catalyst for the isocyanate reaction. More preferably, the polymer of the invention is formed using about 2 weight equivalents of diisocyanate, about 1 weight equivalents of polyether, about 1 weight equivalents of chain extender, and 1-5% catalyst for the isocyanate reaction. The method typically comprises mixing the catalyst with the chain extender and a suitable solvent (i.e. an organic solvent such as acetone) to form a pre-mixture in which the components are typically miscible in the solvent, and then mixing the pre-mixture and polyether-diisocyanate typically until the solvent has substantially or completely evaporated. The polymer may then be transferred to a mould and shaped and cured.

As used herein, the term "narrow molecular weight distribution" refers to a polydispersity index of 1.0-1.2.

As used herein, the term "melt shear" means that the polymer has not undergone melt processing.

As used herein, the term "mouldable" as applied to the polymer of the invention means that the polymer can be poured into a mould for the purpose of shaping an implantable biomaterial. "Shaping" means that the polymer is converted from a liquid state into a solid state, which generally involves removal of solvent and hardening of the polymer. The polymer may be shaped in a mould (often involving heat and pressure), by solvent casting, or by forming the polymer into fibres (for example by electrospinning). The polymer is generally cured during shaping.

As used herein, the term "curing" as applied to the mouldable polymer means heating the polymer to cure the polymer. Generally, this is carried out in a mould during the shaping of the polymer to form the implantable biomaterial. Curing increases hydrogen bonding in the polymer, reduces the level of solvent, and promotes polymerisation. Curing may also be performed at room temperature or by other means (for example chemical curing).

As used herein, the term "diisocyanate" refers to an aromatic or aliphatic diisocyanate. In a preferred embodiment, the diisocyanate is an aromatic diisocyanate, for example toluene diisocyanate, a phenylene diisocyanate, or a methylene diisocyanate (methylene diphenyl diisocyanate). Typically, the aromatic diisocyanate comprises a benzene ring with two isocyanate groups attached to the ring, preferably but not exclusively at the 2, 4 positions. The term may also refer to aliphatic diisocyanates, for example hexamethylene diisocyanate, hydrogenated methylene diphenyl diisocyanate and isophorone diisocyanate. More generally, any diisocyanate useful in preparing polyurethanes and polyurethane-ureas from polyether glycols, diisocyanates and diols or amines can be used in this invention. They include 2,4-toluene diisocyanate, 2,6-toluene diisocyanate ("TDI"), 4,4'-diphenylmethane diisocyanate or ("MDI"), 4,4'-dicyclohexylmethane diisocyanate ("H12MDI"), 3,3'-dimethyl-4,4'-biphenyl diisocyanate ("TODI"), 1,4-benzene diisocyanate, trans-cyclohexane-1,4-diisocyanate, 1,5-naphthalene diisocyanate ("NDI"), 1,6-hexamethylene diisocyanate ("HDI"), 4,6-xylyene diisocyanate, isophorone diisocyanate ("IPDI"), and combinations thereof. MDI, HDI, and TDI are preferred because of their ready commercial availability.

As used herein, the term "polyether" refers to a polymer formed of glycol groups (i.e. a polyoxyalkylene diol or polyol), and includes poly(propylene glycol), poly(ethylene glycol), poly(tetraethylene glycol), poly(tetramethylene glycol), Poly(tetramethylene glycol), Hydroxyl terminated Poly (dimethyl siloxane), Hydroxy terminated polybutadiene, Polybutylene adipate, and Polycaprolactone. The polyol reacts with the diisocyanate to form the linear prepolymer. In one embodiment, the polyol has a polydispersity index of about 1. The polyether employed in the present invention may have a number average molecular weight (Mn) in the range of about 1000 to about 4000, about 2000 to about 4000, about 1000 to about 3000, about 3000 to about 4000, or about 2000 to 3000. In one embodiment, the polyether is not polytrimethylene ether glycol.

As used herein the term "polyether-diisocyanate prepolymer" refers to a prepolymer formed from polyether and diisocyanate molecules, typically having a structure $X_1[Yn]mX_2$, where:

$X_1$ and $X_2$ are each, independently, an (aromatic) diisocyanate, in which $X_2$ is optionally absent;

Y is a polyether; and $Z_1$ and $Z_2$ are each, independently, chain extender molecules; and n and m are each independently a whole number greater than 1

An example is a poly(propylene glycol)-toluene diisocyanate terminated prepolymer. Polyether-diisocyanate polyurethane prepolymer can be manufactured according to literature methods for example [Zhang et al, Progress in Organic Coatings, Vol. 97, August 2016;], and are available commercially (for example polypropylene glycol toluene-2, 4-diisocyanate (PPG-TDI) (Sigma 433497) pre-polymer, Polyether/TDI PU Prepolymer from Exceed Fine Chemicals).

As used herein, the term "chain extender" refers to a molecule having two functional groups, each of which is configured for reacting with an isocyanate group. The functional groups may be each, independently, selected from an amine group (typically a primary amine) and a hydroxyl group (typically a primary hydroxyl group). In one embodiment, the chain extender is an aromatic molecule. In one embodiment, the chain extender comprises a benzene molecule bearing two functional groups. In one embodiment, the functional groups are disposed symmetrically on the aromatic group (for example 1, 4). In one embodiment, the chain extender comprises a benzene diol (preferably a benzene 1,4-diol) and/or p-phenylene diamine, and/or an aminophenol (4-aminophenol). In one embodiment, the chain extender comprises amine and hydroxyl groups. This may involve employing a chain extender that comprises both functional groups, or at least two types of chain extenders, one having one type of functional group (i.e. amine) and the other having a second type of functional group (i.e. hydroxyl). In one preferred embodiment, two chain extenders are employed, namely p-phenyl diamine and hydroquinone (or a hydroquinone derivative having two hydroxyl functional groups).

Diol chain extenders useful in making the polymers used in the invention include ethylene glycol, 1,2-propylene glycol, 1,3-propanediol, 1,4-butanediol, 1,6-hexanediol, diethylene glycol, 2-methyl-1,3-propanediol, 3-methyl-1,5-pentanediol, 2,2-dimethyl-1,3-propanediol, 2,2,4-trimethyl-1,5-pentanediol, 2-methyl-2-ethyl-1,3-propanediol, 1,4-bis (hydroxyethoxy)benzene, bis(hydroxyethylene) terephthalate, hydroquinone bis(2-hydroxyethyl) ether, benzene 1,4-diol and combinations thereof. Preferred are ethylene glycol, 1,2-propylene glycol, 1,3-propanediol, 1,4-butanediol, 1,6-hexanediol, and 2-methyl-1,3-propanediol.

Diamine chain extenders useful in making the polymers used in the invention include 1,2-ethylenediamine, 1,6-hexanediamine, 1,2-propanediamine, 4,4'-methylene-bis(3-chloroaniline) (also known as 3,3'-dichloro-4,4'-diaminodiphenylmethane) ("MOCA" or "Mboca"), dimethylthiotoluenediamine ("DMTDA"), 4,4'-diaminodiphenylmethane ("DDM"), 1,3-diaminobenzene, 1,4-diaminobenzene, 3,3'-dimethoxy-4,4'-diamino biphenyl, 3,3'-dimethyl-4,4'-diamino biphenyl, 4,4'-diamino biphenyl, 3,3'-dichloro-4,4'-diamino biphenyl, and combinations thereof.

In one preferred embodiment, the chain extender comprises benzene 1,4-diol. In one preferred embodiment, the chain extender comprises benzene 1,4-diol and a second chain extender with amino functionality. In an especially preferred embodiment, the chain extender comprises p-phenylene diamine and benzene-1-4-diol, optionally in combination with another chain extender.

As used herein, the term "implantable biomaterial" refers to a synthetic polymer-based implant. It will be appreciated that the implantable biomaterial of the present invention can be any material/implant for which calcification resistance would be desirable. Preferably, the implantable biomaterial (or implantable device) is selected from the group consisting of valves (or parts thereof including a valve leaflet), implantable conduits, heart assist device (such as a ventricular assist device) or part thereof, stents, tissue prosthesis (for example an ENT prosthesis, or cartilage, ligament or tendon prosthesis), catheters, balloons and shunts, or a fibre used to form one of these devices (for example an electrospun fibre). Valves may be any type of valve in the body, for example coronary valves (for example aortic valve, mitral valve, tricuspid valve, or pulmonary valve) or peripheral vasculature valves such as venous valves, urinary valves, oesophageal valves, pyloric valves, gastrointestinal valves, and sphincter valves. In one embodiment, the implantable biomaterial is selected from a heart valve leaflet, an artificial heart, an extracardiac compression device, an intra or extravascular compression device, a heart valve prosthesis, an annuloplasty ring, a dermal graft, a vascular graft, a vascular stent, a structural stent, a vascular shunt, a cardiovascular shunt, a dura mater graft, a cartilage graft, a cartilage implant, a pericardium graft, a ligament prosthesis, a tendon prosthesis, a urinary bladder prosthesis, a pledget, a permanently in-dwelling percutaneous device, a surgical patch, a cardiovascular stent, a coated stent and a coated catheter. More preferably, the device is a heart valve prosthesis. In one embodiment, the implant will include a plurality of cells, which, upon implantation at a surgical site, will proliferate and integrate into the surrounding tissue.

As used herein, the term "valve leaflet" refers to cusps anchored between two chambers of the heart which open and close in response to pressure and volume to facilitate unidirectional blood flow as part of the cardiac cycle. Examples include an aortic valve, mitral valve, tricuspid valve, or pulmonary valve leaflets.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

One aspect of the invention is a polyurethane-urea formulated for the specific application to heart valve leaflets. In one embodiment, the polymer is achieved by reacting a diisocyanate such as 2,4-toluene diisocyanate with a polyether to form a polyether-diisocyanate prepolymer and reacting the prepolymer with one or more chain extenders such as a combination of p-phenylene diamine, benzene-1, 4-diol and 4-aminophenol chain extenders. The equivalent weight ratio for the diisocyanate, polyether and chain extender may be 2:1:1, with the hard segment content typically being approximately 17%.

There are many factors which contribute to good fatigue resistance, but the main requirements are

- a well-defined two-phase morphology consisting of hard segments, comprised of the isocyanate and chain extender, embedded in an elastomeric matrix
- the chemical nature of the reactants
- low free volume content
- the amount of hard segment content In one embodiment of the invention, a linear polymer is created as this possesses less free volume compared with a non-linear polymer and it also allows for phase separation. Preparing polymers from isocyanate containing chemicals requires two functional isocyanate groups and linear polymers are formed when both chemicals have two functional groups as shown in FIG. 1. An isocyanate reacting with a hydroxyl group results in a urethane bond and an isocyanate reacting with an amine group results in a urea bond (FIG. 1). The maximum molecular weight of the polymer occurs when the ratio of the isocyanate groups to the reacting functional groups is one, which it is in the invention. This is also preferable to ensure that there are no free isocyanate groups remaining in the final polymer.

In one embodiment, a prepolymer formed from a polyol, such as poly(propylene glycol), with a polydispersity index of approximately one and 2,4-toluene diisocyanate, is reacted with the chain extenders to form the polymer. This is typically referred to as a "two-shot" process. The main advantage of this is in obtaining a consistent polymer because the polyol is not competing with the chain extenders for the free isocyanate groups. Primary amines have much higher reaction rates than primary hydroxyl groups and so a "one-shot" reaction could result in a very high molecular weight distribution polymer compared with the "two-shot" process. A higher molecular weight distribution could result in oligomers leaching out of the polymer, compromising the biocompatibility, and the resultant polymer would be weaker in terms of its mechanical properties. The molecular weight of the polymer is typically greater than 1000 g/mol in order to ensure good mechanical properties and phase separation. The current invention is not subjected to any thermal process which could affect the molecular weight distribution and the Fourier Transform Infra-red spectroscopy results confirm that the reaction has completed and that there are no free isocyanate groups.

Figure 2:
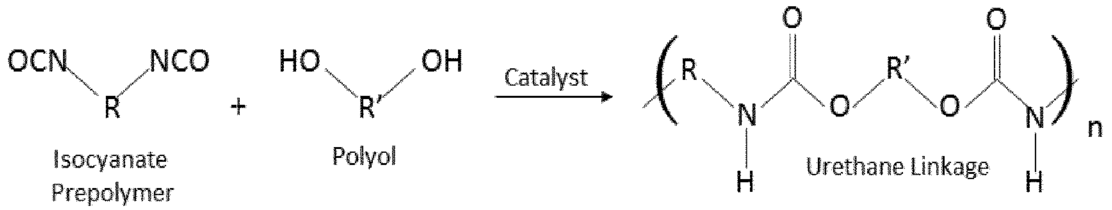
FIG. 2: Hydrogen bonding in polyurethane-urea polymers.
Figure 2:
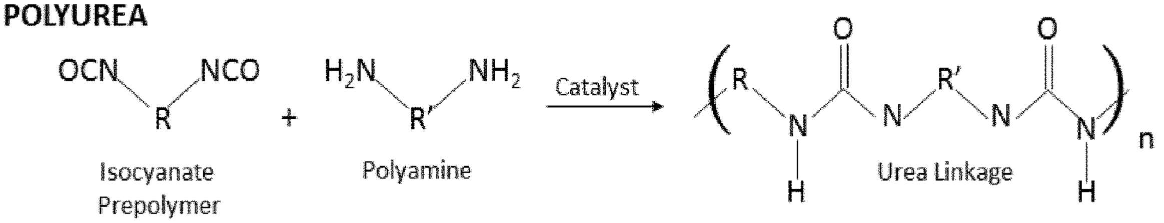

In one embodiment, the current invention uses p-phenylene diamine, benzene-1-4-diol and 4-aminophenol chain extenders in varying ratios to provide the required amount of phase separation through both the stiffness of the chain extender itself, and the functional groups attached to it. These chain extenders are linear aromatic molecules with either primary amine, primary hydroxyl groups or both. Chain extenders can produce either monodentate or bidentate hydrogen bonding (FIG. 2), which helps to increase the elastic modulus of the material as well as acting as a driving force for microphase separation, even when asymmetric diisocyanate molecules, such as 2,4-toluene diisocyanate, are used. The aromatic molecules also improve the biocompatibility.

The resultant polyurethane-urea is a hydrogen bonded, micro-phase separated structure with mechanical properties suitable for a polymer heart valve.

Example 1

A formulation using the following recipe has been created 2 equivalent weights of 2,4-toluene diisocyanate 1 equivalent weight of 2300 g/mol poly(propylene glycol)

0.5 equivalent weight p-phenylene diamine (chain extender)

0.5 equivalent weight of benzene-1,4-diol (chain extender)

3% zinc neodecanoate catalyst

The following weighing, mixing, and evaporation steps are to be performed in a chemical safety cabinet:

In a glass beaker with magnetic stir rod the following are combined: 0.03 g zinc neodecanoate (Shepherd Mirecourt 1364), 0.14 g benzene-1,4-diol (Sigma H17902), and 0.13 g p-phenylene diamine (Sigma 78429). To this beaker 25 ml of acetone is added and the mixture is stirred at ambient temperature on a magnetic stir plate with magnetic stir rod at a speed of 200 RPM for 15 minutes until all contents have become miscible in acetone solution. In a separate glass beaker, 6.18 g of polypropylene glycol toluene-2,4-diisocyanate (PPG-TDI) (Sigma 433497) pre-polymer is measured. The contents of the beaker containing the chain extender are transferred to the beaker with the pre-polymer (PPG-TDI). This mixture is stirred at ambient temperature at 200 RPM until acetone has evaporated. When the mixture has reached an appropriate viscosity (thick jelly consistency) such that the magnetic stir bar can no longer rotate freely, the reacted polymer mixture is transferred into a mould, compressed by a clamp, and cured in an oven at 50 degrees C. for 4.5 hours. After 4.5 hours, the moulds are removed from the oven, allowed to cool to ambient temperature, and samples are removed from the moulds.

The above formulation exhibited a 5% Modulus, Ultimate Tensile Strength and Elongation to Break of 8.8 MPa, 46.5 MPa and 150% when tested at clinically relevant speeds.

Figure 3:
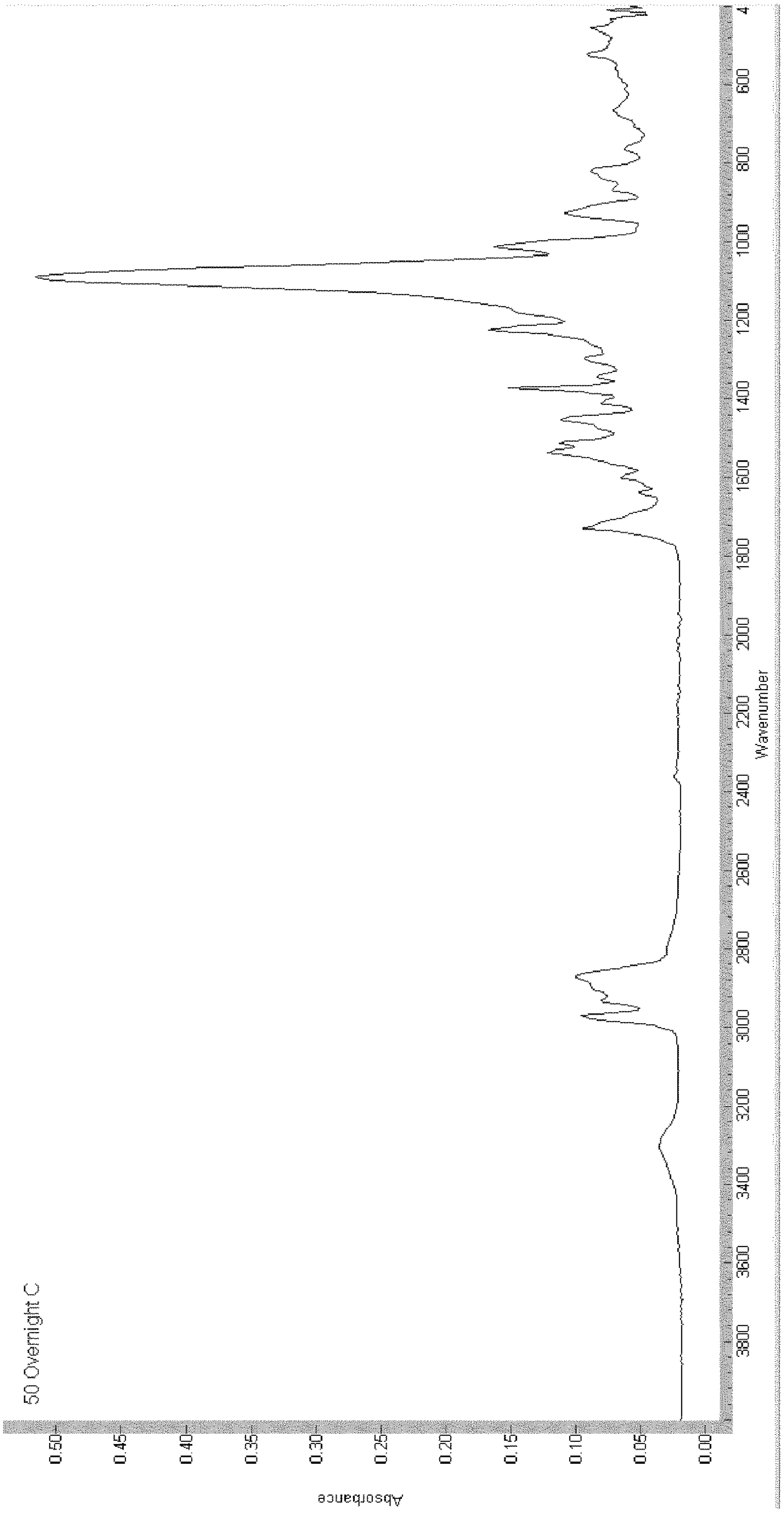
FIG. 3: Differential Scanning Calorimetry scan of polyurethane-urea sample.

The Differential Scanning Calorimetry Heat, Cool and Reheat cycle scan is shown in FIG. 3. The scan shows a crystalline melting endotherm on the initial heat and an absence of a crystallisation exotherm on cooling and a melting endotherm on reheating. This confirms a hydrogen bonded and phase separated structure which is destroyed on melting.

Figure 4:
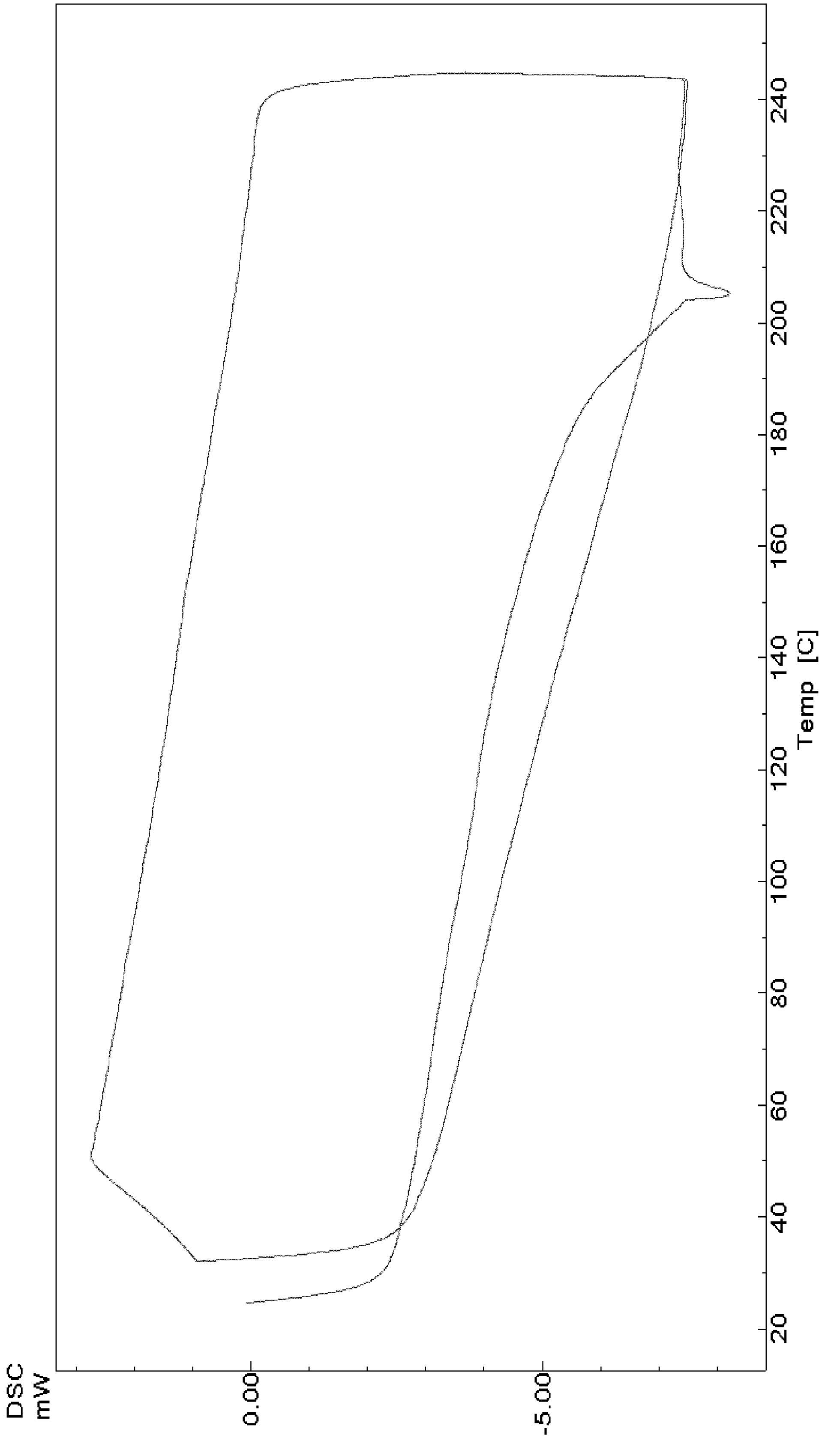
FIG. 4: FTiR scan of polyurethane-urea sample.

The corresponding Fourier Transform Infra-red Spectroscopy (FTiR) scan is shown in FIG. 4. The peak at 1640 cm-1 is indicative of hard segment hydrogen bonding.

Example 2

A formulation using the following constituent parts has been created 2 equivalent weights of 2,4-toluene diisocyanate 1 equivalent weight of 2300 g/mol poly(propylene glycol)

1 equivalent weight Ethanolamine (chain extender)

3% zinc neodecanoate catalyst

The following weighing, mixing, and evaporation steps are to be performed in a chemical safety cabinet:

In a glass beaker with magnetic stir rod the following are combined: 0.0321 g zinc neodecanoate (Shepherd Mirecourt 1364) and 0.1531 ml Ethanolamine (Sigma 411000-100ML). To this beaker 10 ml of acetone is added and the mixture is stirred at ambient temperature on a magnetic stir plate at a speed of 200 RPM for 5 minutes until all contents have become miscible in acetone solution. In a separate glass beaker, 6.20 g of polypropylene glycol toluene-2,4-diisocyanate (PPG-TDI) (Sigma 433497) pre-polymer is measured. The contents of the beaker containing the chain extender are transferred to the beaker with the pre-polymer (PPG-TDI). This mixture is stirred at ambient temperature at 200 RPM until acetone has evaporated. When the mixture has reached an appropriate viscosity (thick jelly consistency) such that the magnetic stir bar can no longer rotate freely, the reacted polymer mixture is transferred into a mould, compressed by a clamp, and cured in an oven at 50 degrees C. overnight. After 18 hours, the moulds are removed from the oven, allowed to cool to ambient temperature, and samples are removed from the moulds.

Example 3

A formulation using the following constituent parts has been created 2 equivalent weights of 2,4-toluene diisocyanate 1 equivalent weight of 2300 g/mol poly(propylene glycol)

1 equivalent weight p-phenylene diamine (chain extender)

3% zinc neodecanoate catalyst

The following weighing, mixing, and evaporation steps are to be performed in a chemical safety cabinet:

In a glass beaker with magnetic stir rod the following are combined: 0.0321 g zinc neodecanoate (Shepherd Mirecourt 1364), and 0.2702 p-phenylene diamine (Sigma 78429). To this beaker 25 ml of acetone is added and the mixture is stirred at ambient temperature on a magnetic stir plate at a speed of 200 RPM for 15 minutes until all contents have become miscible in acetone solution. In a separate glass beaker, 6.18 g of polypropylene glycol toluene-2,4-diisocyanate (PPG-TDI) (Sigma 433497) pre-polymer is measured. The contents of the beaker containing the chain extender are transferred to the beaker with the pre-polymer (PPG-TDI). This mixture is stirred at ambient temperature at 200 RPM until acetone has evaporated. When the mixture has reached an appropriate viscosity (thick jelly consistency) such that the magnetic stir bar can no longer rotate freely, the reacted polymer mixture is transferred into a mould, compressed by a clamp, and cured in an oven at 50 degrees C. for 4.5 hours. After 4.5 hours, the moulds are removed from the moulds.

The hydrogen bonding ration of the polymers were quantified in polymers by taking the sum of the hydrogen bonded peak heights for the amine and carboxyl groups, divided by the sum of all the peak heights from an FTIR spectrum for a given polymerised polyurethane, giving a unitless ratio of hydrogen bonding, which is presented in Table 1 below for the polymers of Examples 1-3. It can be seen that the use of a hydroquinone chain extender in Example 1 provides the highest hydrogen bonding ratio.

TABLE 1

| Polymer | Hydrogen bonding ratio |
|---|---|
| Example 1 | 0.77 |
| Example 2 | 0.66 |
| Example 3 | 0.70 |

Example 4

A formulation using the following constituent parts is made according to the methods described above:

2 equivalent weights of 2,4-toluene diisocyanate 1 equivalent weight of 2300 g/mol poly(propylene glycol)

1 equivalent weight of benzene-1,4-diol (chain extender)

3% zinc neodecanoate catalyst

Example 5

A formulation using the following constituent parts is made according to the methods described above:

2 equivalent weights of 2,4-toluene diisocyanate 1 equivalent weight of 2300 g/mol poly(ethylene glycol)

0.5 equivalent weight p-phenylene diamine (chain extender)

0.5 equivalent weight of benzene-1,4-diol (chain extender)

3% zinc neodecanoate catalyst

Example 6

A formulation using the following constituent parts is made according to the methods described above:

2 equivalent weights of 4,4'-diphenylmethane diisocyanate or ("MDI"), 1 equivalent weight of 2300 g/mol poly(propylene glycol)

0.5 equivalent weight p-phenylene diamine (chain extender)

0.5 equivalent weight of benzene-1,4-diol (chain extender)

3% zinc neodecanoate catalyst

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An implant comprising a shaped and cured implantable flexible biomaterial formed by:

providing a polyether-diisocyanate prepolymer formed by reacting a polyether with a toluene diisocyanate;

reacting the prepolymer with one or more chain extender molecules, said one or more chain extender molecules comprising benzene-1,4-diol and a chain extender molecule having amine functionality; optionally, in which the chain extender molecule having amine functionality is p-phenylene diamine;

wherein reacting the prepolymer with the one or more chain extender molecules form a mouldable polymer selected from a polyurethane polymer, a polyurethane-urea polymer, or a polyurethane-urea block copolymer; and shaping and curing the mouldable polymer to form the implantable biomaterial, wherein the mouldable polymer exhibits the hydrogen bonded microphase separated morphology.

2. The implant of claim 1, in which the polyether is selected from the group consisting of: poly(propylene glycol); poly(ethylene glycol); poly(tetraethylene glycol); poly(tetramethylene glycol); Poly(tetramethylene glycol); Hydroxyl terminated Poly(dimethyl siloxane); Hydroxy terminated polybutadiene; Polybutylene adipate; and Polycaprolactone.

3. The implant of claim 1, in which the toluene diisocyanate is 2,4 toluene diisocyanate.

4. The implant of claim 1, in which:

the prepolymer is reacted with two chain extender molecules in which the two chain extender molecules are benzene-1,4-diol and p-phenylene diamine; and the polyether is selected from poly(propylene glycol), poly(ethylene glycol), poly(tetraethylene glycol) and poly(tetramethylene glycol).

5. The implant of claim 1, in which a weight ratio of toluene diisocyanate, polyether and chain extender in the mouldable polymer is 2-6:1-3:1-3.

6. The implant of claim 1, in which the mouldable polymer is shaped in an implantable biomaterial shaped mould.

7. The implant of claim 1, in which the mouldable polymer is cured in an implantable biomaterial shaped mould.

8. The implant of claim 1, wherein the implant is selected from a valve or valve leaflet, implantable conduit, heart assist device, stent, tissue prosthesis, catheter, balloon, shunt, or a fibre.

9. The implant of claim 1, in which the implant is a heart valve.

10. The implant of claim 1, in which the implant is a percutaneous delivered heart valve.

11. The implant of claim 1, wherein the implant is selected from an artificial heart, an extracardiac compression device, an intra or extravascular compression device, a heart valve prosthesis, an annuloplasty ring, a dermal graft, a vascular graft, a vascular stent, a structural stent, a vascular shunt, a cardiovascular shunt, a dura mater graft, a cartilage graft, a cartilage implant, a pericardium graft, a ligament prosthesis, a tendon prosthesis, a urinary bladder prosthesis, a pledget, a permanently in-dwelling percutaneous device, a surgical patch, a cardiovascular stent, a coated stent and a coated catheter.

12. The implant of claim 1, in which the implant is a heart valve leaflet.

13. A heart valve leaflet formed by:

providing a polyether-diisocyanate prepolymer formed by reacting a polyether with a toluene diisocyanate;

reacting the prepolymer with one or more chain extender molecules to form a mouldable polymer selected from a polyurethane polymer, a polyurethane-urea polymer, and a polyurethane-urea block copolymer; and shaping and curing the mouldable polymer to form an implantable biomaterial, characterised in that the one or more chain extender molecules comprise benzene-1,4-diol and the mouldable polymer exhibits a microphase separated morphology.

14. A heart valve leaflet formed by:

providing a polyether-diisocyanate prepolymer formed by reacting a polyether with a toluene diisocyanate;

reacting the prepolymer with one or more chain extender molecules to form a mouldable polymer selected from a polyurethane polymer, a polyurethane-urea polymer, and a polyurethane-urea block copolymer; and shaping and curing the mouldable polymer to form an implantable biomaterial, characterised in that the one or more chain extender molecules consist of benzene-1,4-diol and a chain extender having amine functionality, and the mouldable polymer exhibits a microphase separated morphology.

15. The implant of claim 1, wherein the prepolymer is reacted with two chain extender molecules, said two chain extender molecules comprising benzene-1,4-diol and a chain extender molecule having amine functionality.

* * * * *